(12) United States Patent
Matsumoto

(10) Patent No.: US 7,216,981 B2
(45) Date of Patent: May 15, 2007

(54) OPHTHALMOLOGIC APPARATUS

(75) Inventor: Kazuhiro Matsumoto, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 606 days.

(21) Appl. No.: 10/833,644

(22) Filed: Apr. 27, 2004

(65) Prior Publication Data
US 2004/0218145 A1 Nov. 4, 2004

(30) Foreign Application Priority Data
May 1, 2003 (JP) .............................. 2003-126517

(51) Int. Cl.
*A61B 3/10* (2006.01)
*A61B 3/14* (2006.01)

(52) U.S. Cl. ..................... 351/205; 351/206; 351/214

(58) Field of Classification Search ................ 351/200, 351/205, 206, 214
See application file for complete search history.

(56) References Cited

U.S. PATENT DOCUMENTS 4,102,563 A  7/1978 Matsumura et al. ........ 351/207
6,361,167 B1  3/2002 Su et al. ..................... 351/206
6,409,341 B1  6/2002 Goldfain et al. ............ 351/205

FOREIGN PATENT DOCUMENTS

FR        2 828 396       2/2003
WO        WO 01/89374    11/2001

*Primary Examiner*—Ricky Mack
*Assistant Examiner*—Jack Dinh
(74) *Attorney, Agent, or Firm*—Morgan & Finnegan LLP

(57) ABSTRACT

There is provided an ophthalmologic apparatus that prevents ghost light from generating. In the ophthalmologic apparatus, on an optical path commonly used for an eye fundus illumination optical system and an image taking optical system including an image taking diaphragm, an objective lens for forming an image of the image taking diaphragm onto an anterior ocular segment of an eye to be examined is provided. The objective lens is formed such that the entire light beam from the center of the image taking diaphragm is substantially perpendicularly incident thereon. The objective lens is a refractive index distributed lens in which a refractive index is high in a vicinity of an optical axis and reduces as a distance from the optical axis increases.

4 Claims, 5 Drawing Sheets

OPHTHALMOLOGIC APPARATUS

BACKGROUND OF THE INVENTION

1. Field of the Invention

The present invention relates to an ophthalmologic apparatus used in an ophthalmologic doctor's office, or used for a group medical examination or the like.

2. Related Background Art

Up to now, an objective lens commonly used for both an illumination optical system and an image taking optical system is provided in an ophthalmologic apparatus. A black point is provided in the illumination optical system in order that reflection light caused by reflecting illumination light on the objective lens is prevented from appearing on an eye fundus image to form a ghost image, and also from mixing into measurement light to reduce measurement precision.

In particular, in the case of a double scanning type laser scanning ophthalmoscope, the black point for suppressing the formation of the ghost image resulting from the reflection light on an optical member cannot be disposed. Therefore, instead of using a refractive optical member such as a lens, a reflective optical member such as a mirror is used.

Even in an ocular refractive power measuring apparatus such as an autorefractometer, the black point is provided in a projection system in order to prevent measurement index projection light from being reflected on the objective lens. In addition, the objective lens is tilted so as not to affect the measurement precision by the reflection light.

However, in the above-mentioned conventional examples, it is difficult to completely remove ghost light with the black point. In addition, a problem in that the shadow of the black point reflects on the eye fundus image to reduce an image quality is caused.

Further, when the ghost light is removed, it is necessary to provide the objective lens with an antireflection film having a high performance, leading to a problem in that parts become expensive.

In particular, in the case of the double scanning type laser scanning ophthalmoscope, a reflective optical system is complex and hard to adjust. In addition, there is a problem in that a size of the apparatus increases as compared with the case using a lens.

SUMMARY OF THE INVENTION

The present invention has been made to solve the above-mentioned problems. Therefore, an object of the present invention is to provide an ophthalmologic apparatus that prevents reflection light on an objective lens from becoming improper light to affect a taken image or a measurement value and thus can obtain an eye fundus image having a preferable image quality or the measurement value with high precision.

To attain the above-mentioned object, according to the present invention, there is provided an ophthalmologic apparatus. In the ophthalmologic apparatus, on an optical path commonly used for an eye fundus illumination optical system and an image taking optical system including an image taking diaphragm, an objective lens for forming an image of the image taking diaphragm onto an anterior ocular segment of an eye to be examined is provided. The objective lens is formed such that the entire light beam from the center of the image taking diaphragm is substantially perpendicularly incident thereon. The objective lens is a refractive index distributed lens in which a refractive index is high in a vicinity of an optical axis and reduces as a distance from the optical axis increases.

DESCRIPTION OF THE PREFERRED EMBODIMENTS

Figure 1:
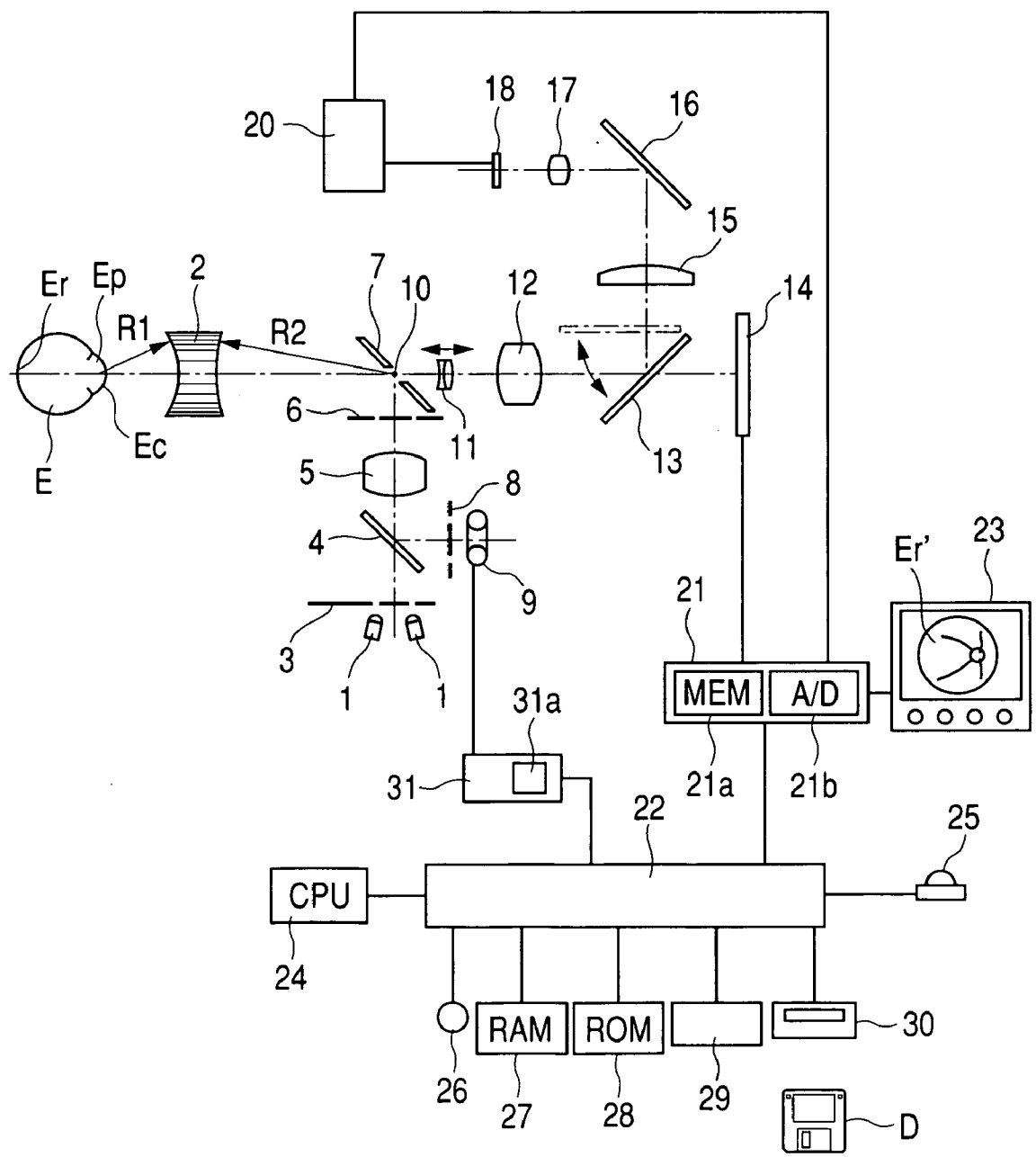
FIG. 1 is a structural diagram showing an eye fundus camera according to a first embodiment of the present invention.

The present invention will be described in detail based on embodiments as shown in the drawings.

FIG. 1 is a structural diagram showing an eye fundus camera according to a first embodiment of the present invention. A diaphragm 3 having a ring opening, an optical path splitting mirror 4 that transmits infrared light and reflects visible light, a relay lens 5, a diaphragm 6 having a ring opening, and a holed mirror 7 having an opening formed in an central portion are disposed in order on an optical path from an observation infrared light source 1 to an objective lens 2 opposed to an eye to be examined E. A diaphragm 8 having a ring opening and an image taking light source 9 composed of a stroboscopic tube are disposed on an optical path in the light incident direction of the optical path splitting mirror 4. The diaphragms 3 and 8 are substantially conjugate with the position of a pupil Ep of the eye to be examined E with respect to the objective lens 2 and the relay lens 5. The diaphragm 6 is substantially conjugate with a cornea Ec of the eye to be examined E with respect to the objective lens 2.

An image taking diaphragm 10 is provided in the opening of the holed mirror 7. A focal lens 11 which is movable on an optical path, an image taking lens 12, a liftable mirror 13, and an image pickup unit 14 are disposed in order on the optical path behind the holed mirror 7. A field lens 15, a mirror 16, an imaging lens 17, and an observation television camera 18 are disposed on an optical path in the light reflection direction of the liftable mirror 13.

An output of the television camera 18 is connected with an image board 21 through a signal processing unit 20 and an output of the image pickup unit 14 is also connected therewith. An output of the image board 21 is connected with a system bus 22 and a television monitor 23. The image board 21 includes an image memory 21a and an A/D converter 21b. The system bus 22 is connected with a CPU 24, an operating unit 25, an image pickup switch 26, a RAM 27, a ROM 28, a keyboard 29, a recording unit 30, and an image taking light source controlling unit 31 including a capacitor 31a.

In eye fundus observation and alignment, an infrared light flux emitted from the observation infrared light source 1 is transmitted through the ring opening of the diaphragm 3, the optical path splitting mirror 4, the relay lens 5, and the opening of the diaphragm 6 and is reflected on the opening of the holed mirror 7 to illuminate an eye fundus Er of the eye to be examined E through the objective lens 2. Reflection light on the eye fundus Er is transmitted through the objective lens 2, the image taking diaphragm 10 provided in the opening of the holed mirror 7, the focal lens 11, and the image taking lens 12. Then, the reflection light is bent by the liftable mirror or optical path changing mirror 13, transmitted through the field lens 15, bent by the mirror 16, transmitted through the imaging lens 17, and imaged onto the observation television camera 18.

The output of the observation television camera 18 is converted into a video signal through the signal processing unit 20 and the image board 21. Therefore, an eye fundus image is displayed on a screen of a television monitor 23. While observing the image, an examiner operates the operating unit 25 so as to move the focal lens 11 in the optical path direction, thereby performing focusing on the eye fundus Er.

When the image pickup switch 26 is pressed after confirming that the lens is not misfocused, the liftable mirror 13 is removed from the optical path and the image taking light source 9 emits flash light. A light flux from the image taking light source 9 passes through the opening of the diaphragm 8, is reflected on the optical path splitting mirror 4, and travels on the same optical path as the observation light flux to illuminate the eye fundus Er. Reflection light on the eye fundus Er passes through the objective lens 2, the image taking diaphragm 10, the focal lens 11, and the image taking lens 12, and is imaged onto the image pickup unit 14. Therefore, an eye fundus image Er' is temporarily stored in the image memory 21a of the image board 21. Then, the eye fundus image Er' is converted into an image recording format. The converted eye fundus image Er' is recorded in the recording unit 30 and displayed on the television monitor 23.

The objective lens 2 is disposed between the image taking diaphragm 10 and the eye to be examined E. A second surface of the objective lens 2 on the image taking diaphragm 10 side is a concave spherical surface having a curvature radius R2 with the center of the image taking diaphragm 10 used as the center of curvature. The image taking diaphragm 10 forms an image in a conjugate relation with the pupil Ep of the eye to be examined E with respect to the objective lens 2. A first surface of the objective lens 2 on the eye to be examined E side is a concave spherical surface having a curvature radius R1 with the imaging point set as the center of curvature. Therefore, the entire light passing through the center of the image taking diaphragm 10 is perpendicularly incident on the first surface and the second surface of the objective lens 2. The entire light reflected on the first surface and the second surface returns to the optical path in which the light is incident.

Figure 2:
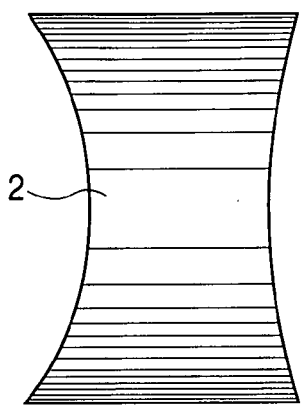
FIG. 2 is an explanatory view showing an objective lens.

As shown in FIG. 2, the refractive index of glass composing the objective lens 2 is highest in the vicinity of the optical axis and gradually reduces toward the circumference. A portion in which a pitch is narrow has a high refractive index and a portion in which a pitch is wide has a low refractive index.

Figure 3:
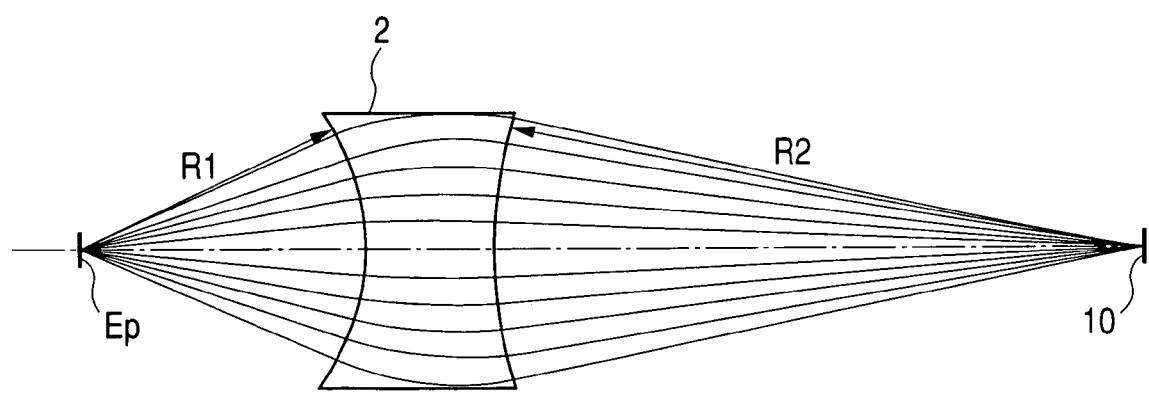
FIG. 3 is an explanatory view showing imaging of a pupil.

FIG. 3 shows a state in which a light beam having exited from the center of the pupil Ep of the eye to be examined E is condensed at the center of the image taking diaphragm 10. This is different from the case of the general lens. The light beam is gradually bent not on the surfaces of the objective lens 2 but in the inner portion of the objective lens 2.

Figure 4:
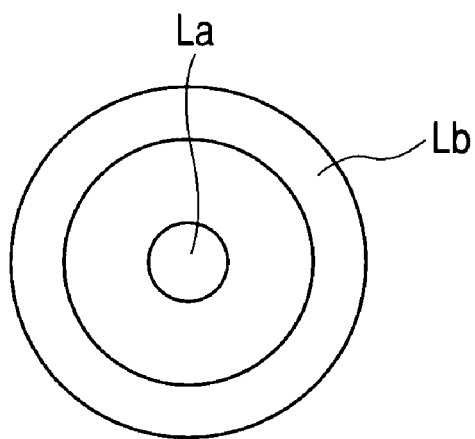
FIG. 4 is an explanatory view showing a diaphragm.

FIG. 4 is a sectional view showing an image taking light flux La and an illumination light flux Lb near the image taking diaphragm 10. An image through the diaphragm 3 having the ring opening is formed near the image taking diaphragm 10, so that the illumination light flux Lb and the image taking light flux La are separated from each other. Therefore, of the illumination light flux Lb, the light reflected on the first surface or the second surface of the objective lens 2 all returns to a position substantially symmetrical to the exit position. That is, even when the light from the region corresponding to the illumination light flux Lb as shown in FIG. 4 is reflected on the respective surfaces of the objective lens 2, the light returns to the region corresponding to the illumination light flux Lb again and does not enter the region corresponding to the image taking light flux La. In other words, the reflection light caused by reflecting the illumination light flux Lb on the objective lens 2 does not overlap with the image taking light flux La. Therefore, a ghost image is not formed on a taken image.

Design Example 1 below is directed to the case where the refractive index of the objective lens 2 at the center thereof is set to 1.83 and Design Example 2 below is directed to the case where the refractive index of the objective lens at the center thereof is set to 1.88. As described above, a shape of the objective lens 2 is determined according to the arrangement. Therefore, the shape is common to Design Example 1 and Design Example 2.

First surface: curvature radius R1=−48.7
Second surface: curvature radius R2=114.1
Center thickness: 24

Provided that the refractive index is expressed as a function of a distance r from the optical axis using $n(r) = n_0 + C_1 \times r^2 + C_2 \times r^4 + C_3 \times r^6 + C_4 \times r^8$, coefficient values in each case are as follows.

DESIGN EXAMPLE 1

$n_0 = 1.83$
$C_1 = -1.029 \times 10^{-3}$
$C_2 = 5.540 \times 10^{-7}$
$C_3 = -2.675 \times 10^{-10}$
$C_4 = 7.837 \times 10^{-14}$

DESIGN EXAMPLE 2

Figure 5:
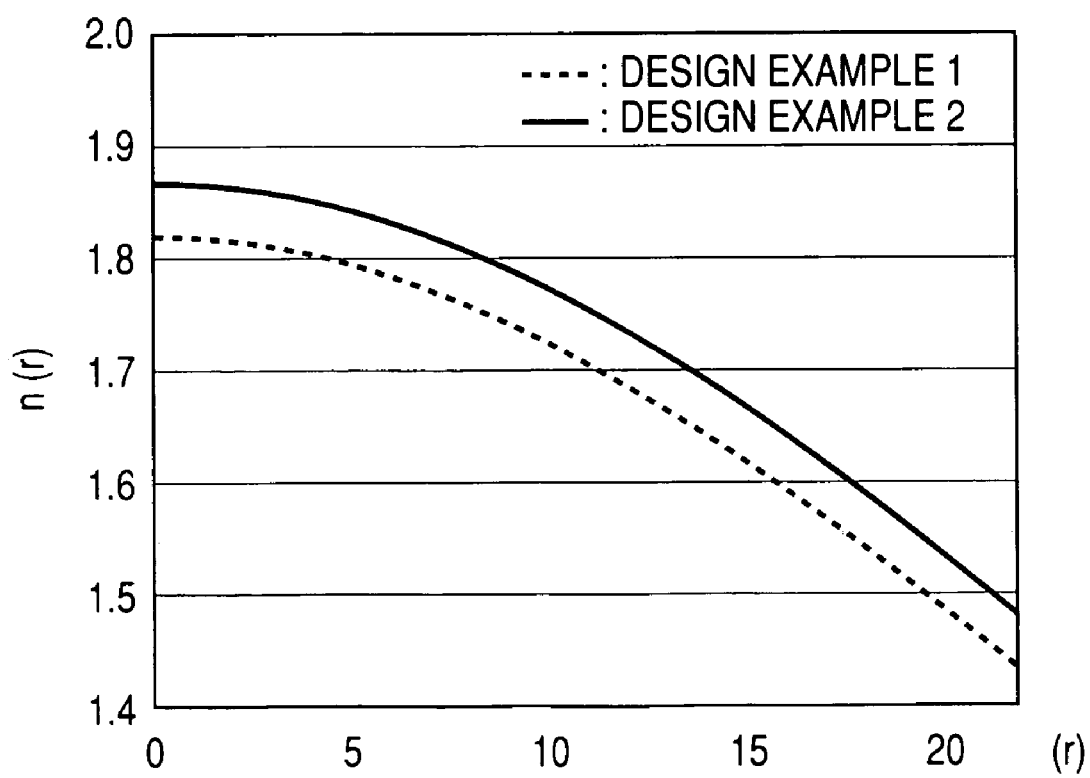
FIG. 5 is a graph showing a refractive index distribution.

$n_0 = 1.88$
$C_1 = -1.046 \times 10^{-3}$
$C_2 = 5.632 \times 10^{-7}$
$C_3 = -2.718 \times 10^{-10}$
$C_4 = 7.949 \times 10^{-14}$ FIG. 5 is a graph showing a refractive index distribution expressed by the above-mentioned expression. The abscissa indicates a distance from the optical axis and the ordinate indicates a refractive index. In Design Example 1, a refractive index distribution with the refractive index at the center set to 1.83 is obtained. In Design Example 2, a refractive index distribution with the refractive index at the center thereof set to 1.88 is obtained. In the case of Design Example 1, the refractive index at the center portion is equal to that of OHARA glass (S-LAH55) produced by OHARA INC. At a distance of about 20 mm from the center, the refractive index is about 1.49 equivalent to that of OHARA glass (S-FSL5) produced by OHARA INC.

In the case of Design Example 2, the refractive index at the center portion is 1.88 equivalent to that of OHARA glass (S-LAH58) produced by OHARA INC. At a distance of about 20 mm from the center, the refractive index is about 1.52 equivalent to that of OHARA glass (S-BSL7) produced by OHARA INC.

The objective lens 2 has a shape of a double-concave lens. However, it functions as a convex lens having a focal distance of 38.5 mm because of the refractive index distribution described above. Therefore, the objective lens 2 forms an image of the pupil Ep and an image of the image taking diaphragm 10 at 2-fold imaging magnification.

Figure 6:
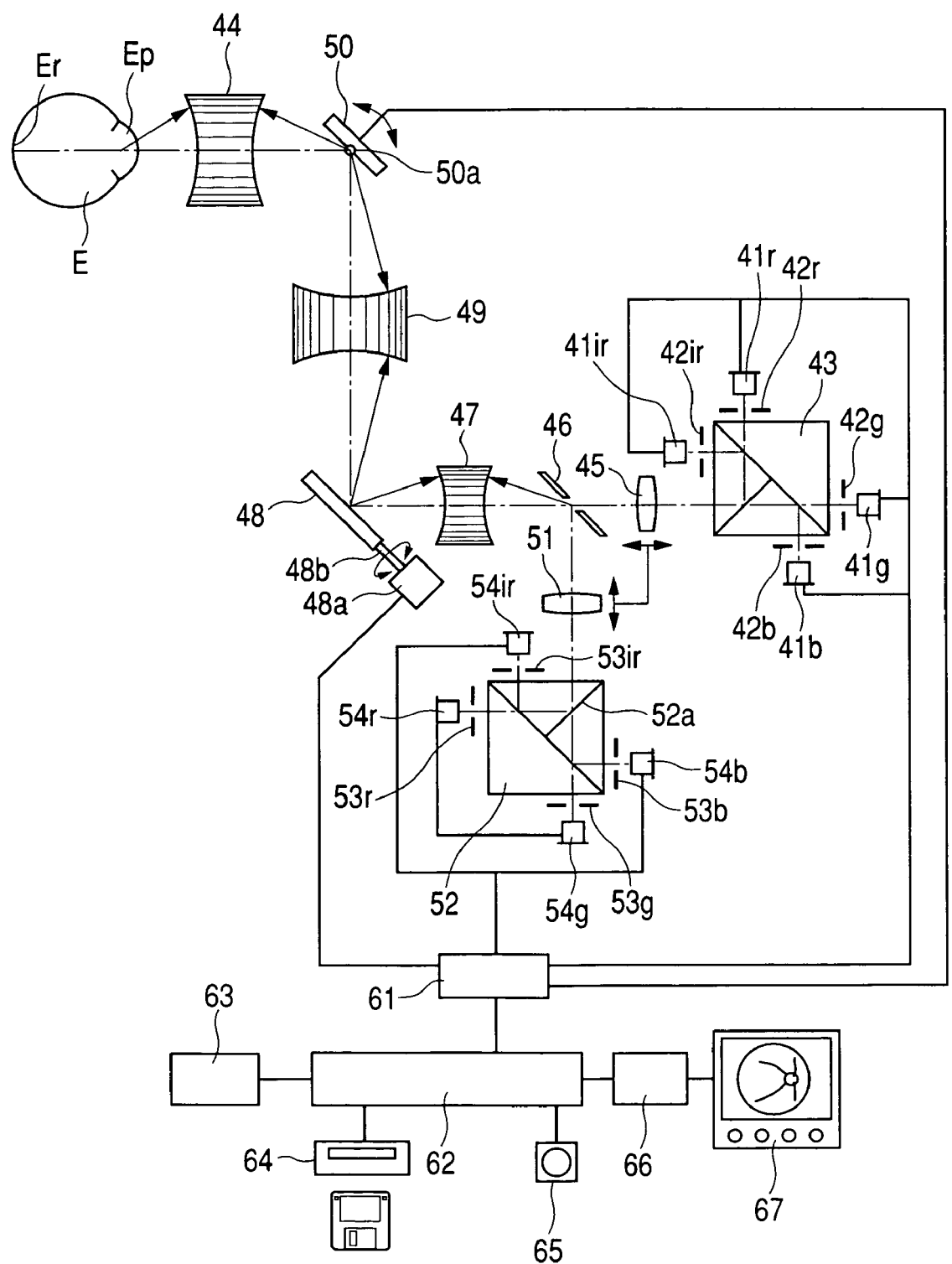
FIG. 6 is an explanatory diagram showing an eye fundus camera according to a second embodiment of the present invention.

FIG. 6 is a structural diagram showing a second embodiment in the case where the lens of the present invention is applied to a laser scanning ophthalmoscope. Infrared light (780 nm), red light (633 nm), green light (566 nm), and blue light (488 nm) which are emitted from laser light sources 41ir, 41r, 41g, and 41b are allowed to enter a wavelength dividing prism 43 through respective corresponding confocal diaphragms 42ir, 42r, 42g, and 42b. A focal lens 45, a holed mirror 46, a relay lens 47, a galvano-mirror 48 which is driven by a drive unit 48a and used for main scanning, a relay lens 49, and a galvano-mirror 50 which is driven by a drive unit 50a and used for sub scanning are disposed on an optical path from the wavelength dividing prism 43 to an objective lens 44. Therefore, a laser projection optical system is constructed.

A focal lens 51 and a wavelength dividing prism 52 are disposed in the light reflection direction of the holed mirror 46. Confocal diaphragms 53ir, 53r, 53g, and 53b and photo detectors 54ir, 54r, 54g, and 54b are disposed on optical paths. Therefore, a light receiving optical system is constructed.

Outputs of the photo detectors 54ir, 54r, 54g, and 54b are connected with a scanning control circuit 61. The scanning control circuit 61 performs driving control of the galvano-mirrors 48 and 50, light emission control of the laser light sources 41ir, 41r, 41g, and 41b, and conversions of signals from the photo detectors 54ir, 54r, 54g, and 54b into digital image data. Further, the scanning control circuit 61 is connected with a CPU 63, a recording unit 64, an image pickup switch 65, and a video board 66 through a system bus 62. The output of the video board 66 is connected with a television monitor 67.

In the above-mentioned structure, the holed mirror 46, the galvano-mirror 48 for main scanning, and the galvano-mirror 50 for sub scanning are disposed substantially conjugate with the pupil Ep of the eye to be examined E. A first surface of the objective lens 44 for imaging on the eye to be examined E side is a concave spherical surface in which the center of the pupil Ep is set as the center of curvature. A second surface of the objective lens 44 on the galvano-mirror 50 side is a concave spherical surface in which an intersection of the galvano-mirror 50 and the optical axis is set as the center of curvature. As in the first embodiment, the objective lens 44 is a refractive index distributed lens in which the refractive index gradually reduces from the vicinity of the optical axis to the circumference.

The objective lens 44 has a shape of a double-concave lens. However, it functions as a convex lens. It addition, as in the objective lens 44, each of the relay lenses 47 and 49 has a concave spherical surface in which the intersection of the galvano-mirror 48 or 50 and the optical axis or the center of an opening of the holed mirror 46 is set as the center of curvature. Therefore, as in the objective lens 44, each of the relay lenses 47 and 49 is composed of a refractive index distributed lens in which the refractive index gradually reduces from the vicinity of the optical axis to the circumference.

Each of the relay lenses 47 and 49 has a shape of a double-concave lens. However, each functions as a convex lens. Therefore, of the light fluxes having exited from the opening of the holed mirror 46, the light reflected on the relay lenses 47 and 49 and the objective lens 44 is all prevented from returning to the opening of the holed mirror 46. Thus, there is no case where the light is incident on the light receiving optical system to form a ghost image that reduces an image quality.

Figure 7:
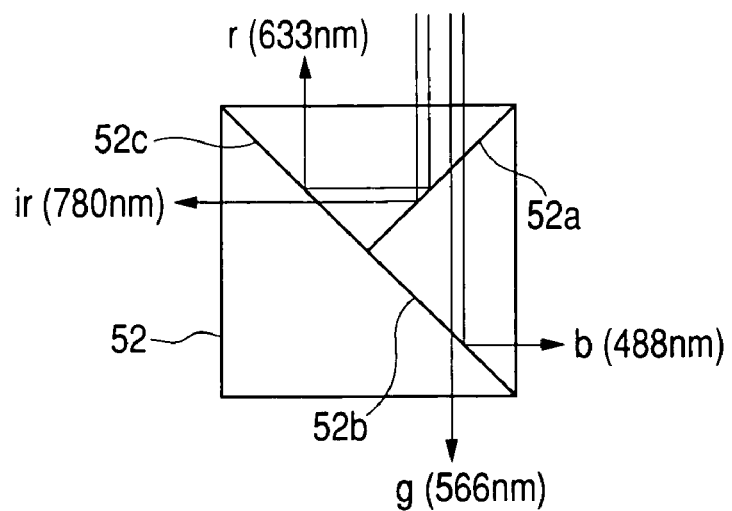
FIG. 7 is an explanatory view showing a prism.

FIG. 7 is an explanatory view for wavelength separation of the wavelength dividing prism 52. A reflective surface 52a reflects red light and infrared light, each of which has a wavelength of 600 nm to 900 nm and transmits blue light and green light, each of which has a wavelength of 400 nm to 600 nm. A reflective surface 52b reflects blue light of 400 to 500 nm and transmits green light. A reflective surface 52c reflects red light of 600 to 700 nm and transmits infrared light of 700 nm or more.

As described above, light sources to be used are the laser light sources 41ir, 41r, 41g, and 41b that respectively emit infrared light having a wavelength of 780 nm, red light having a wavelength of 633 nm, green light having a wavelength of 566 nm, and blue light having a wavelength of 488 nm. In the case of infrared fluorescent image taking, it is necessary to receive fluorescence having a band width of about 800 nm to 900 nm. Therefore, it is desirable that the reflective surface 52a of the wavelength dividing prism 52 reflects light of up to about 900 nm. When the wavelength dividing prism 52 is used, spectroscopy is possible in a small space, so that a size of the apparatus can be reduced.

First, the eye to be examined E is observed using infrared light and alignment is performed. The confocal diaphragm 42ir is illuminated with the infrared light emitted from the infrared light source 41ir. The image of the confocal diaphragm 42ir is reflected on the color separating prism or the wavelength dividing prism 43, transmitted through the focal lens 45, the opening of the holed mirror 46, and the relay lens 47, and reaches the galvano-mirror 48 for main scanning.

The galvano-mirror 48 rotatably oscillates about a rotational axis 48b by the drive unit 48a. Therefore, the illumination light (infrared light) is scanned in a direction perpendicular to the paper surface and reaches the galvano-mirror 50 for sub scanning through the relay lens 49. The galvano-mirror 50 rotatably oscillates about a rotational axis 50a for sub scanning. Then, the infrared light is transmitted through the objective lens 44 to two-dimensionally scan the eye fundus Er through the pupil Ep of the eye to be examined E.

The reflection light on the eye fundus Er is transmitted through the pupil Ep again and is reflected downward on a reflective surface of the holed mirror 46 through the objective lens 44, the galvano-mirror 50, the relay lens 49, the galvano-mirror 48, an the relay lens 47. Then, the light is transmitted through the focal lens 51 and is subjected to spectroscopy by the wavelength dividing prism 52. The processed light is imaged onto the confocal diaphragm 53ir and received in the photo detector 54ir. The image is converted into an electrical signal by the photo detector 54ir, inputted to the scanning control circuit 61, and converted into a digital image signal. Then, the digital image signal is converted into a video signal by the video board 66 and displayed on the television monitor 67.

While observing the eye fundus image displayed on the television monitor 67, an image-taking person operates an operating unit so as to move the focal lenses 45 and 51, thereby performing image taking preparations such as focusing and alignment adjustment. When the focal lenses 45 and 51 are moved in conjunction with each other, the substantial conjugation between the confocal diaphragms 42ir, 42r, 42g, and 42b for illumination and the confocal diaphragms 53ir, 53r, 53g, and 53b for light reception is always maintained.

After the completion of the image taking preparations is ensured, the image-taking person presses the image pickup switch 65. When the image pickup switch 65 is pressed, each of the laser light sources 41r, 41g, and 41b emits a light beam. The light beams emitted from light sources are combined by the wavelength dividing prism 52 and travel on the same optical path as in the infrared light to two-dimensionally scan the eye fundus Er. As in the case of the infrared light, the reflection light beams return to the same optical path as at the incidence and are reflected on a peripheral portion of the holed mirror 46. Then, the reflection light beams transmit through the focal lens 51 and are subjected to spectroscopy by the wavelength dividing prism 52. The processed light beams are imaged onto the confocal diaphragms 53r, 53g, and 53b and received in the photo detectors 54r, 54g, and 54b.

Electrical signals generated in the photo detectors 54r, 54g, and 54b are converted into digital image data by the scanning control circuit 61. The digital image data is displayed as a still image on the television monitor 67 through the video board 66 and recorded in the recording unit 64, thereby completing image taking. Thus, the objective lens 44 and the relay lenses 47 and 49 can be disposed on the optical path commonly used for both illumination and light reception, so that a size of the entire optical system can be reduced.

Figure 8:
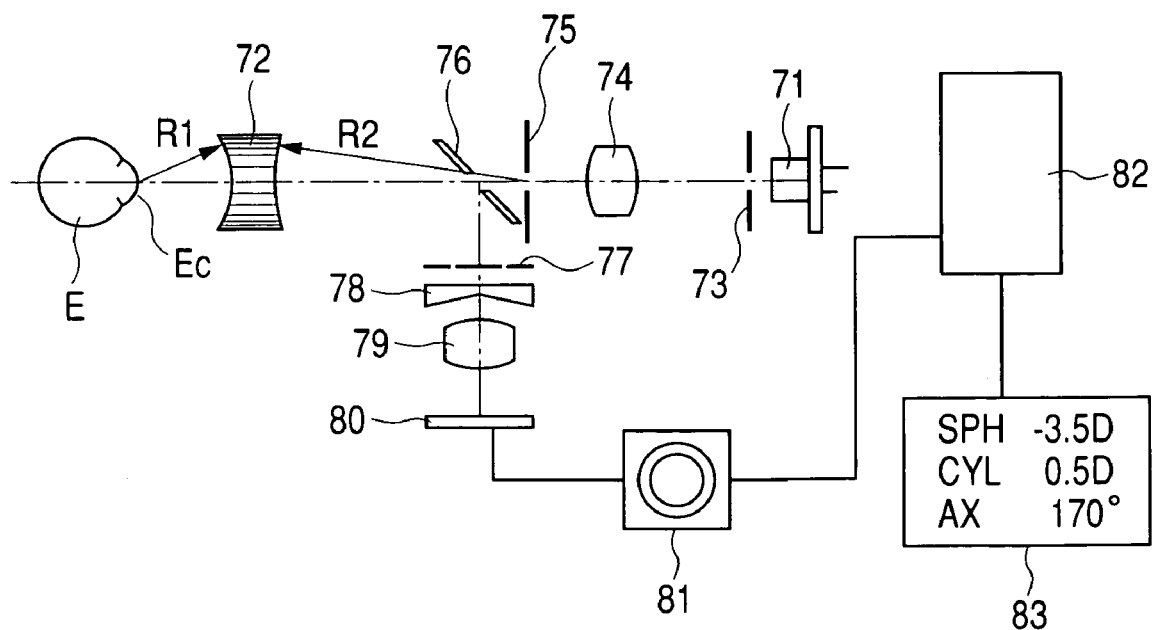
FIG. 8 is a structural diagram showing an autorefractometer according to a third embodiment of the present invention.

FIG. 8 is a structural diagram showing a third embodiment in the case where the lens of the present invention is applied to an autorefractometer. A projection index 73, a lens 74, a diaphragm 75, and a holed mirror 76 are disposed on an optical path from a light source 71 to an objective lens 72. A pupil diaphragm 77, a prism 78, a lens 79, and a two-dimensional area sensor 80 are disposed in the light reflection direction of the holed mirror 76. An output of the two-dimensional area sensor 80 is connected with a display unit 83 through an image board 81 and a calculation unit 82. An output of the calculation unit 82 is connected with the light source 71.

In measurement, the projection index 73 is illuminated with light emitted from the light source 71. An index image of the projection index is transmitted through lens 74 and an opening of the diaphragm 75 and then transmitted through an opening of the holed mirror 76. Then, the index image reaches the eye fundus Er of the eye to be examined E through the objective lens 72. The reflection light on the eye fundus Er of the eye to be examined E is transmitted through the objective lens 72 again, is reflected on a peripheral portion of the holed mirror 76, transmitted through an opening of the pupil diaphragm 77, and deflected by the prism 78. Then, the light is transmitted through the lens 79 and forms a ring image on the two-dimensional area sensor 80.

The image board 81 stores the index image as digital image data. The calculation unit 82 analyzes a shape of the index image, calculates spherical refraction power, astigmatism power, and an astigmatism angle, and causes the display unit 83 to display a calculation result.

In such a structure, both the diaphragm 75 and the diaphragm 75 are substantially conjugate with the pupil of the eye to be examined. The projection light flux and the receiving light flux are separated from each other. A second surface of the objective lens 72 on the diaphragm 75 side is a concave spherical surface in which an intersection of the diaphragm 75 and the optical axis is the center of curvature. A first surface of the objective lens 72 on the eye to be examined E side is a concave spherical surface in which an intersection of the pupil of the eye to be examined and the optical axis is the center of curvature. As in the above-mentioned embodiments, the objective lens 72 is a refractive index distributed lens in which the refractive index gradually reduces from the optical axis to the circumference. Thus, even when the objective lens 72 has a shape of a double-concave lens, it functions as a convex lens.

In the case where such an objective lens 72 is used, even when the projection light flux passing through the diaphragm 75 is reflected on any surface of the objective lens 72, the projection light flux is transmitted through the opening of the holed mirror 76 and returns to the opening of the holed mirror 75. Therefore, the projection light flux does not reach the two-dimensional area sensor 80, with the result that it does not become ghost light that affects a measurement value.

As described above, according to the ophthalmologic apparatus in the present invention, the reflection light on the objective lens is prevented from becoming improper light to affect a taken image or a measurement value. Therefore, an eye fundus image having a preferable image quality or the measurement value with high precision can be obtained. It is unnecessary to use a black point. Therefore, the number of parts can be reduced, an adjustment mechanism can be omitted, and a size of the illumination optical system can be reduced.

What is claimed is:

1. An ophthalmologic apparatus, comprising:
an eye fundus illumination optical system for illuminating an eye fundus;
an image taking optical system including an image taking diaphragm, for taking an image of the eye fundus; and
an objective lens for forming an image of the image taking diaphragm onto an anterior ocular segment of an eye be examined, the objective lens being disposed on an optical path common to the eye fundus illumination optical system and the image taking optical system,
wherein the objective lens is formed such that an entire light beam from a center of the image taking diaphragm is substantially perpendicularly incident thereon and the objective lens is a refractive index distributed lens in which a refractive index is high in a vicinity of an optical axis and reduces as a distance from the optical axis increases.

2. An ophthalmologic apparatus according to claim 1, wherein the ophthalmologic apparatus comprises an eye fundus camera.

3. An ophthalmologic apparatus according to claim 1, wherein the ophthalmologic apparatus comprises a laser scanning ophthalmoscope.

4. An ophthalmologic apparatus according to claim 1, wherein the ophthalmologic apparatus comprises an autorefractometer.

* * * * *